US005968329A

United States Patent [19]
Anderson et al.

[11] Patent Number: 5,968,329
[45] Date of Patent: Oct. 19, 1999

[54] INTERCHANGEABLE MULTIPLE TEST SYSTEM FOR PORTABLE ANALYZER

[75] Inventors: Carter R. Anderson, Eagan; Jon J. Crumm, St. Louis Park; Martin G. Hieb, Minneapolis; Kee Van Sin, Lino Lakes, all of Minn.

[73] Assignee: Diametrics Medical, Inc., Roseville, Minn.

[21] Appl. No.: 08/851,970

[22] Filed: May 6, 1997

[51] Int. Cl.⁶ .................................................. G01N 27/26
[52] U.S. Cl. ........................................ 204/402; 422/82.01
[58] Field of Search ................................. 204/400, 402, 204/403, 409; 205/775; 422/82.01, 82.02

[56] References Cited

U.S. PATENT DOCUMENTS

| | | | |
|---|---|---|---|
| 4,228,814 | 10/1980 | Luethi et al. | 134/58 R |
| 4,786,394 | 11/1988 | Enzer et al. | 204/401 |
| 4,871,439 | 10/1989 | Enzer et al. | 204/401 |
| 5,004,583 | 4/1991 | Guruswamy et al. | 422/58 |
| 5,232,667 | 8/1993 | Hieb et al. | 422/82.4 |
| 5,325,853 | 7/1994 | Morris et al. | 600/308 |

FOREIGN PATENT DOCUMENTS 0 520 443 A2   of 0000   European Pat. Off. .

OTHER PUBLICATIONS

"The GEM Story", Mallinckrodt Sensor Systems, MSS 213, Nov. 1993, 10M.
"The GEM Central Data Management System", Jul. 1994, Mallinckrodt Sensor Systems.

Primary Examiner—Robert Warden
Assistant Examiner—Alex Noguerola
Attorney, Agent, or Firm—Nikolai, Mersereau & Dietz, P.A.

[57] ABSTRACT

A portable clinical system for providing a rapid electrochemical analysis of biological sera of interest at the point-of-care using a portable analyzer unit and a multi-sensor electrochemical plug-in cartridge analyzing system is disclosed which features a plug-in module including a reusable sensor cartridge having an inlet port for receiving a sample, an outlet drain port and array of self-calibrating electrochemical sensors, a plurality of electrical interfaced terminals for interfacing with the portable analyzer unit. An integral flushing system is provided for cleaning and allowing recalibration of the sensor between sample analyses. Connection devices on the analyzer unit and plug-in multi-use test module are provided for removably attaching the module to the analyzer unit. The connection devices are configured to receive a single-use sensor cartridge interchangeably and without modification with said plug-in multi-use test module.

13 Claims, 10 Drawing Sheets

INTERCHANGEABLE MULTIPLE TEST SYSTEM FOR PORTABLE ANALYZER

BACKGROUND OF THE INVENTION

I. Field of the Invention

The present invention is directed generally to portable diagnostic or electro-analytical systems that make in vitro electrochemical determinations based on fluid biological samples extracted from patients and characteristically analyzed for concentrations of specific electroactive species. The system employs a cartridge containing a bank of sensors for the pertinent electroactive species which provide input in the form of analog electrical signals for the relevant determinations. More particularly, the instant invention is concerned with a portable diagnostic or analytical instrument that interfaces and uses cartridges selected from single-use cartridges interchangeably with a modular multiple-use cartridge system to make rapid, accurate point-of-care determinations at low cost and requiring only a relatively low skill level to operate successfully.

II. Related Art

The measurement of certain physical/chemical characteristics or conditions of the blood can be quite important with respect to evaluating the condition of a patient in a variety of clinical situations. The partial pressures of $O_2$ and $CO_2$, pH, together with the measurement of certain ions, such as $Ca^{++}$ and/or $K^+$, provide important indications of the efficiency of the blood/gas exchange occurring in the lungs of the patient, relative acid/base balance in the concentration of certain indicative ion species in the blood, respectively. Hematocrit is also an important determination. These measurements are particularly critical in life-threatening circumstances.

While formerly all such analyzers of the class employed to make such determinations were costly, permanently installed devices in the hospital laboratories which required highly-trained, skilled technicians to operate them. More recently, portable units have become available which make fairly rapid analyses in the operating room, such as during open heart surgery, the intensive care unit and the emergency room. In these areas, of course, immediate diagnostic and therapeutic decisions are often required. The data from blood gas, electrolyte and certain other tests forms the basis for such reactions.

Systems are also available which utilize a plurality of cartridge-mounted sensors to sequentially make many sample determinations. Examples of such systems are shown in U.S. Pat. Nos. 4,786,394 and 4,871,439 to Enzer et al and, more recently, reusable, multiple sample testing systems are shown in European Patent Application 0 520 443 A2 to Betts et al. and in certain Mallinckrodt product information material dated 1993–1995. Thus, while single-use and multiple-use systems exist, the per test cost has remained relatively high in comparison with laboratory systems and the versatility associated with the ability to accommodate both single-use and multi-use cartridges interchangeably as heretofore not been available.

Accordingly, it is a primary object of the present invention to provide a portable, point-of-care analytical system that interchangeably accommodates single-use cartridges and a multi-use cartridge module.

Another object of the present invention is to provide a portable point-of-care analytical instrument that accommodates both single-use cartridges and a multi-use cartridge test module interchangeably without modification.

Yet another object of the present invention is to provide a plug-in multi-use sensor cartridge module for a portable, point-of-care blood analysis instrument which uses no more power than a single-use cartridge.

Other objects and advantages of the present invention will become apparent to those skilled in the art upon familiarization with the specification, drawings and claims contained herein.

SUMMARY OF THE INVENTION

In accordance with the present invention, added versatility is achieved in a portable analytical device where rapid and accurate chemical analysis is desired from blood gas samples or the like by the provision of a simple snap fitting or plug-in multi-test unit or module capable of sequentially processing a large number of samples and sequentially cleaning and recalibrating the sensors between the sequential samples tested. The modular unit is interchangeable with a single-use disposable plug-in cartridge unit that uses the same sensor system and is designed to share the same plug-in connection on the portable analyzer instrument. Speed and accuracy of obtaining test results is preserved with respect to both and the simplicity of the multi-use modular unit reduces the cost per test significantly.

The multi-use unit includes a relatively hollow support housing on which the analytical sensor cartridge is mounted in a manner which enables it to make electrical plug-in connection with the portable analytical unit in a manner identical to that for a single-use cartridge. The multi-use modular unit further includes a source of clean fluid utilized for flushing or washing away each previous sample and replacing it with fluid usable to allow automatic recalibration of the sensors for the next sample. In the detailed embodiment, this system utilizes a reciprocating finger pump connected between a reservoir source of fluid material housed in the modular unit and the sample inlet port of the cartridge unit. The flushing and calibration solution delivery system further includes a resilient closure means which protects the cartridge sample charging port between uses. The multi-use modular cartridge unit further includes an outlet or drain effluent connection which leads to a separate storage container or reservoir for used samples and flushing solution.

The sensor bank configuration and circuitry of the multiple-use cartridge is identical with that for a single-use cartridge and switching between the two requires no modification or further adaptation of the analytical instrument. Cartridge sensors may be of a type illustrated in U.S. Pat. No. 5,325,853 to Morris et al. and sensor temperature may be controlled in accordance with U.S. Pat. No. 5,232,667 to Hieb et al, both of which are hereby incorporated by reference for any purpose.

It should be noted that in accordance with the present invention the multi-use modular system uses no additional electrical power and requires no circuitry modification or other changes in the system. Also the system has no moving parts other than the hand pump and seal.

BRIEF DESCRIPTION OF THE DRAWINGS

In the drawings wherein like numerals designate like parts throughout the same.

DETAILED DESCRIPTION

The present invention adds versatility to a portable analytical point-of-care device without sacrificing the repeatable accuracy and speed of obtaining analytical results or making modifications to an existing system also dedicated to single-use, disposable cartridge analysis. The multi-use modular unit can be interchangeably plugged in or snap-fit with a single-use cartridge in the same instrument. This provides a further ability to reuse a sensor system known to have this capability and thereby reducing the cost of analyzing each sample. Times during the day when use is less frequent, the multiple-use modular system can simply be disconnected and single-use cartridges utilized instead. The modular system contains just enough flushing and recalibration fluid and used material storage capacity to complete the designated number of sample tests.

Figure 1:
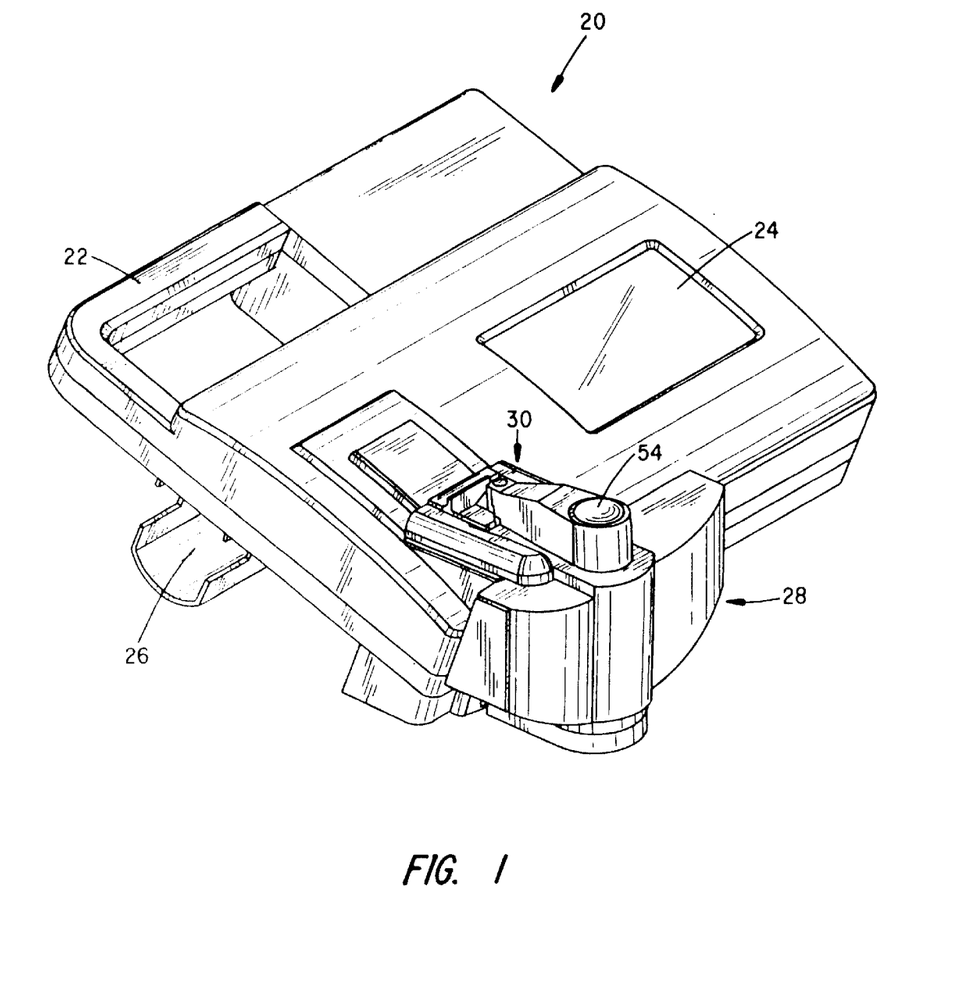
FIG. 1 is a perspective view of a portable analytical device including a detachable multi-use cartridge test module assembled to the device.

With respect to the detailed description, the particular embodiments shown and described in the specification are presented as examples only and are not meant to place any limitations on the inventive concept. In describing the present illustrative detailed embodiment, FIG. 1 of the drawings depicts a perspective view of a portable analytical device in accordance with the invention generally at 20. The device includes an external housing 21 which forms a carrying handle 22, an opening covered with a transparent cover 24 houses an LCD or other type human readable output display. The system further includes a battery case at 26, a printer system (not shown) and a multiple-use test cartridge system or module 28 is shown attached and addressing a cartridge receptacle receiving area generally 30.

Figure 2:
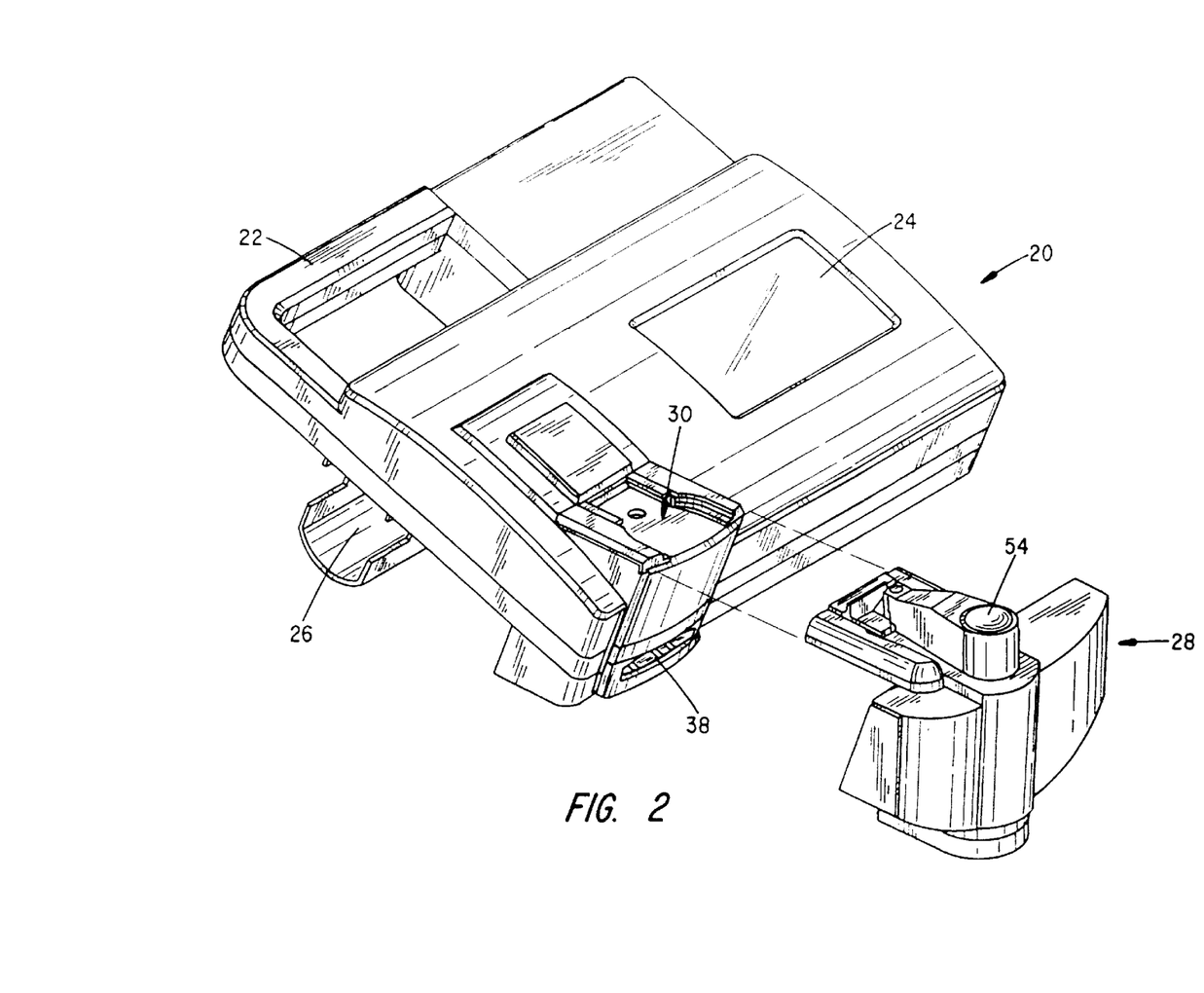
FIGS. 2 and 3 depict the portable analytical device of FIG. 1 showing the multiple-use cartridge test module detached from the portable analytical device.
Figure 3:
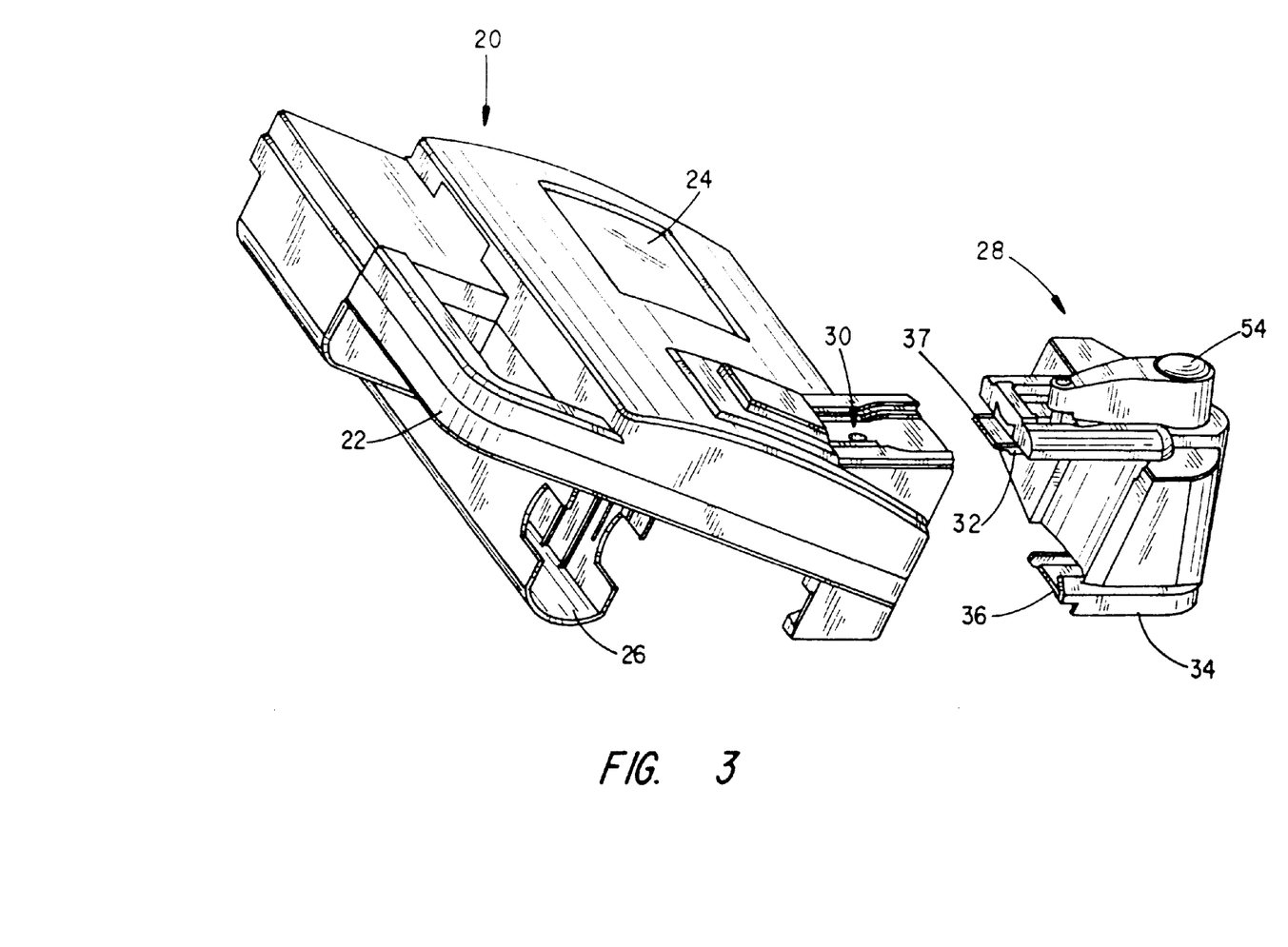

FIGS. 2 and 3 show the multi-use test cartridge module detached from the main analyzer. The multi-use system is designed with a removable plug-in or snap-fitting member 32 (FIG. 3 and 6) and a lower stabilizing support footing member 34 which has an integral forwardly protruding segment 36 designed to be inserted and held in stabilizing relation by a matching recess or receptacle 38 (FIG. 2) in the lower part of the housing 21 such that when snapped in, the system 28 is stably mounted to the analyzer 20. The cartridge plug interface is shown at 37 and is identical with single-use embodiments.

Figure 6:
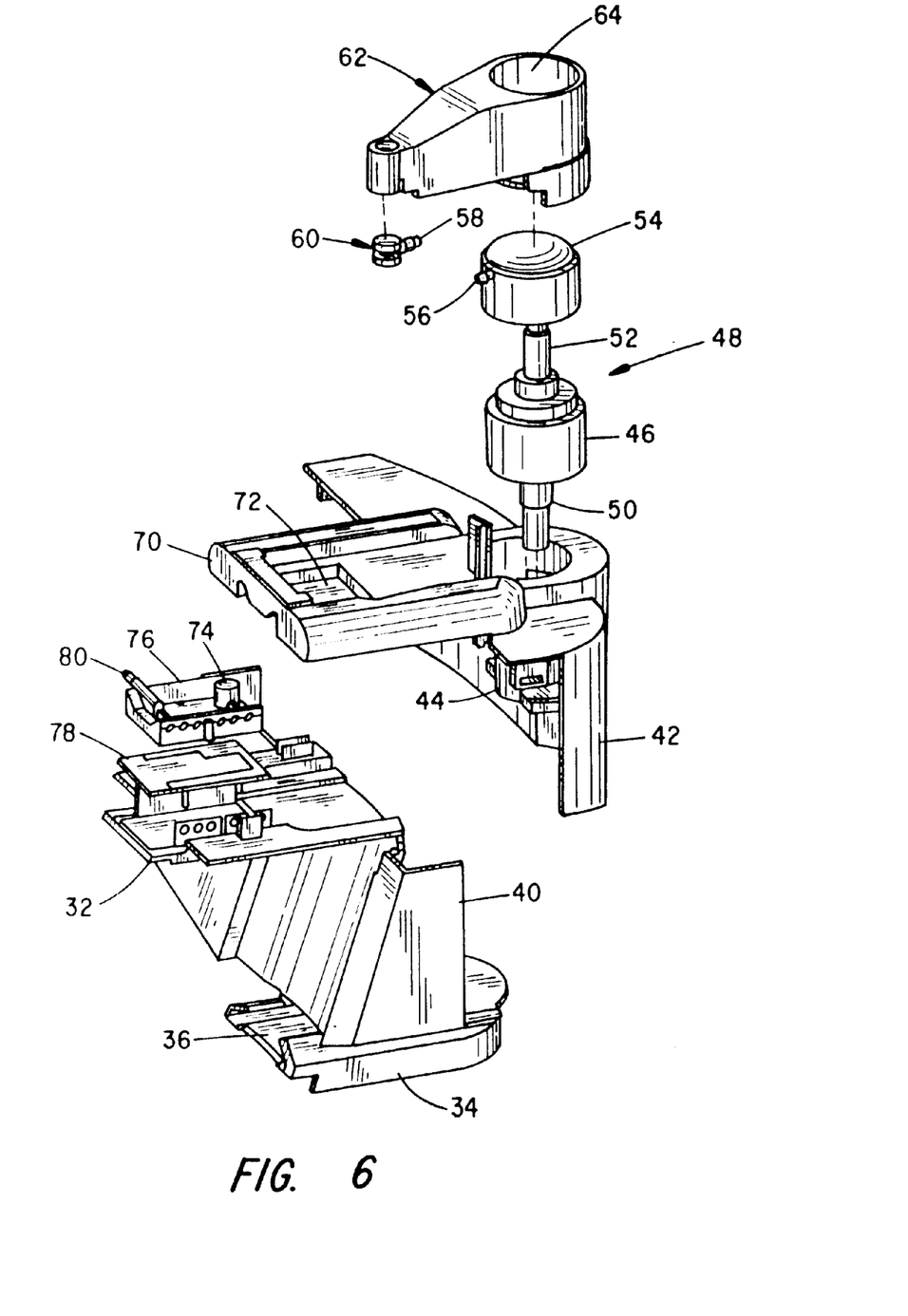
FIG. 6 is an exploded or blown apart view of the multi-use cartridge test module of the invention.

The component parts making up the multiple-use system 28 are best introduced and depicted with respect to the exploded view of FIG. 6 in which a hollow lower housing is depicted as being made up of a shaped front section 40 and a shaped rear section 42 with the lower stabilizing support pedestal mounted to the section 40. It will be appreciated that exact configurations of these parts are dictated by the ability to mold intricate shapes of polymeric parts and the system is designed to be constructed of low-cost but relatively versatile moldable polymer materials chemically compatible with all aspects of the system including the samples to be tested. Thus, the housing portions 40 and 42, together, describe the hollow internal volume which is utilized to contain both a source of rinsing and calibration fluid and a container for storing used fluid and sample materials from previous runs.

The shaped member 42 further contains an integral internal housing member 44 designed to receive the body section 46 of a reciprocal pumping device 48 as by being threadably attached and fixed therein. The pump itself may be of a spring-loaded, hand-operated type utilized for the push button spraying of cleaning materials such as window cleaners or the like, and such devices are well known. The pumping device 48 also includes an inlet or suction pipe 50, which is attached as by flexible plastic tubing to a source of fluid (not shown).spring biased push button pumping plunger 52, push button 54 and outlet nozzle 56. The outlet nozzle 56 is connected to the inlet of a cartridge flushing nozzle system 60 also by a section of flexible hollow tubing such as polyethylene tubing (not shown). The source of flushing and calibrating fluid in the form of a flexible reservoir (not shown) is housed in the hollow lower housing.

The upper portion of the pumping device 48 nests into a hollow recess in the under side of a shaped spray arm 62 with the push button 54 exposed and slightly protruding through the upper side of opening 64 to be operated from above as assembled. The shaped member 42 also carries a shaped hollow upper housing 70 which contains an opening 72 which, in turn, allows access by the flush nozzle 60 to the sample and flushing port 74 of the cartridge chamber 76 which is fixed to the sensor carrying board member 78. The board member 78 is, in turn, fixed to the member 32.

As seen particularly in FIG. 3, the sensor board protrudes beyond the member 32 at 37 to make the required electrical connection in the recess 30 when the multi-use modular system 28 is attached to the portable analytical device 20. The multi-use cartridge fixed in the system 28 is made up of the combination of the chamber 76 and the sensor board or card 78 which also contains all of the cartridge circuitry. An effluent or outlet port 80 is provided to drain displaced samples and rinse/calibration material from previous tests. The outlet nozzle or port 80 is connected by tubing similar to the inlet tubing to an affluent collection reservoir (not shown) which also, as indicated above, is located in the body of the system formed by the shaped segments 40 and 42.

Figure 7A:
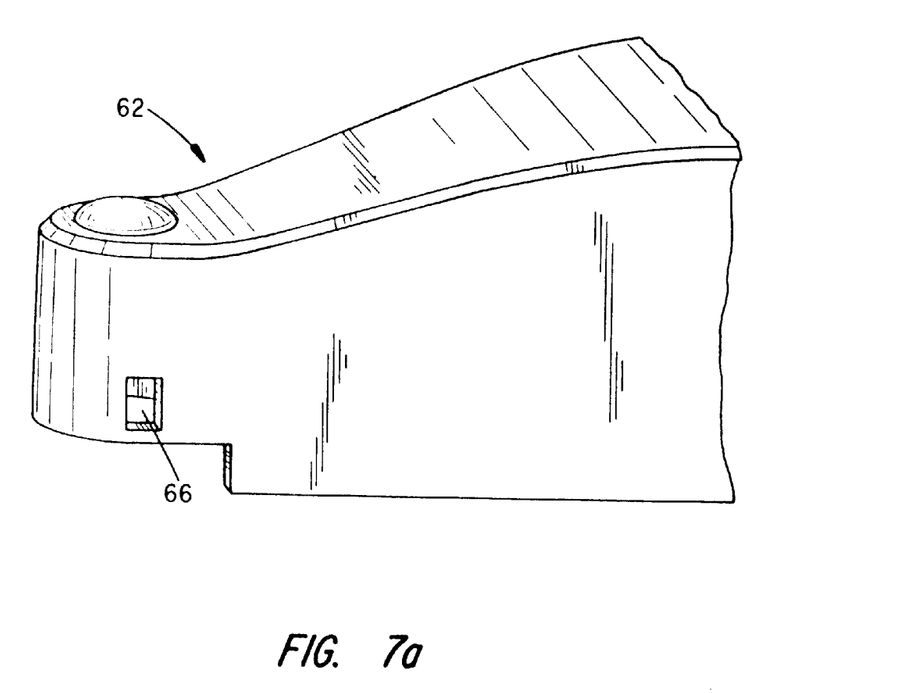
FIGS. 7a and 7b are greatly enlarged fragmentary views that depict details of the rinse arm system.
Figure 7B:
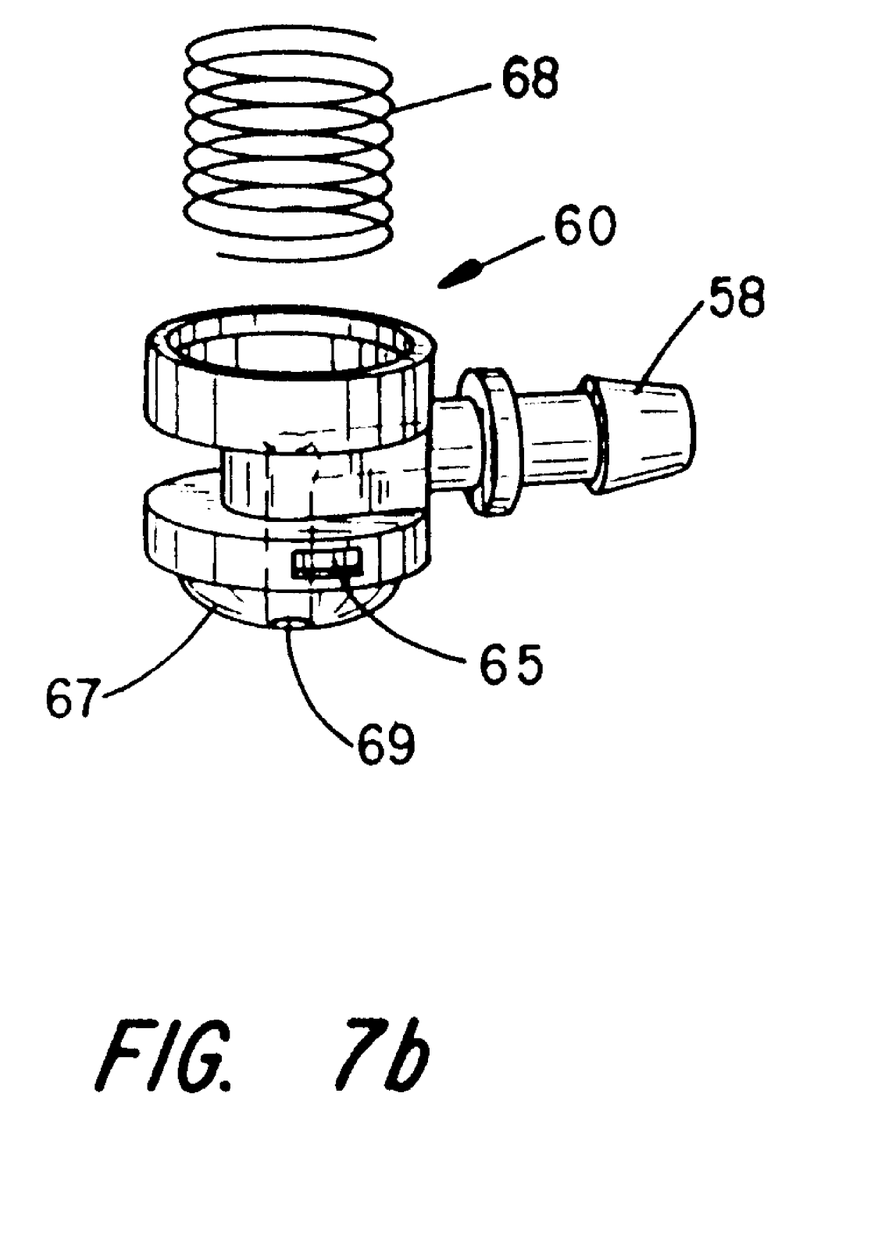

Further details of the arm and nozzle system are revealed by the greatly enlarged fragmentary perspective views of FIGS. 7a and 7b where the flush/calibration nozzle 60 is shown to have a pair of protruding side tabs, one of which is shown at 65 which are designed to snap-fit and be carried in slots in the arm member 62, one of which is shown at 66. Resiliency is provided by a compression spring 68 which urges the nozzle 60 downward in the arm 62.

Figure 4A:
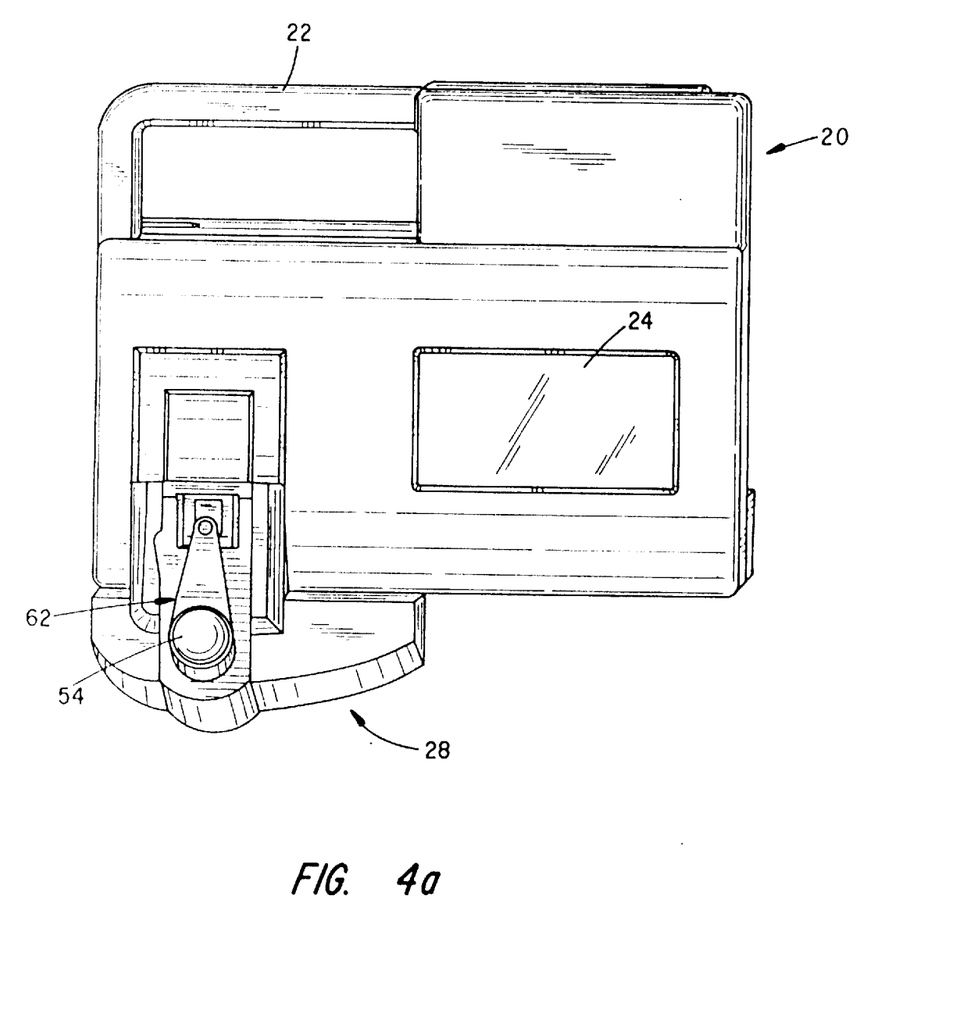
FIGS. 4a and 4b depict top views of the assembled system of FIG. 1 portraying the rinse arm of the multiple-use test cartridge module in a rinsing or sample port sealing position and an alternate position shifted away to allow a sample to be injected, respectively.
Figure 4B:
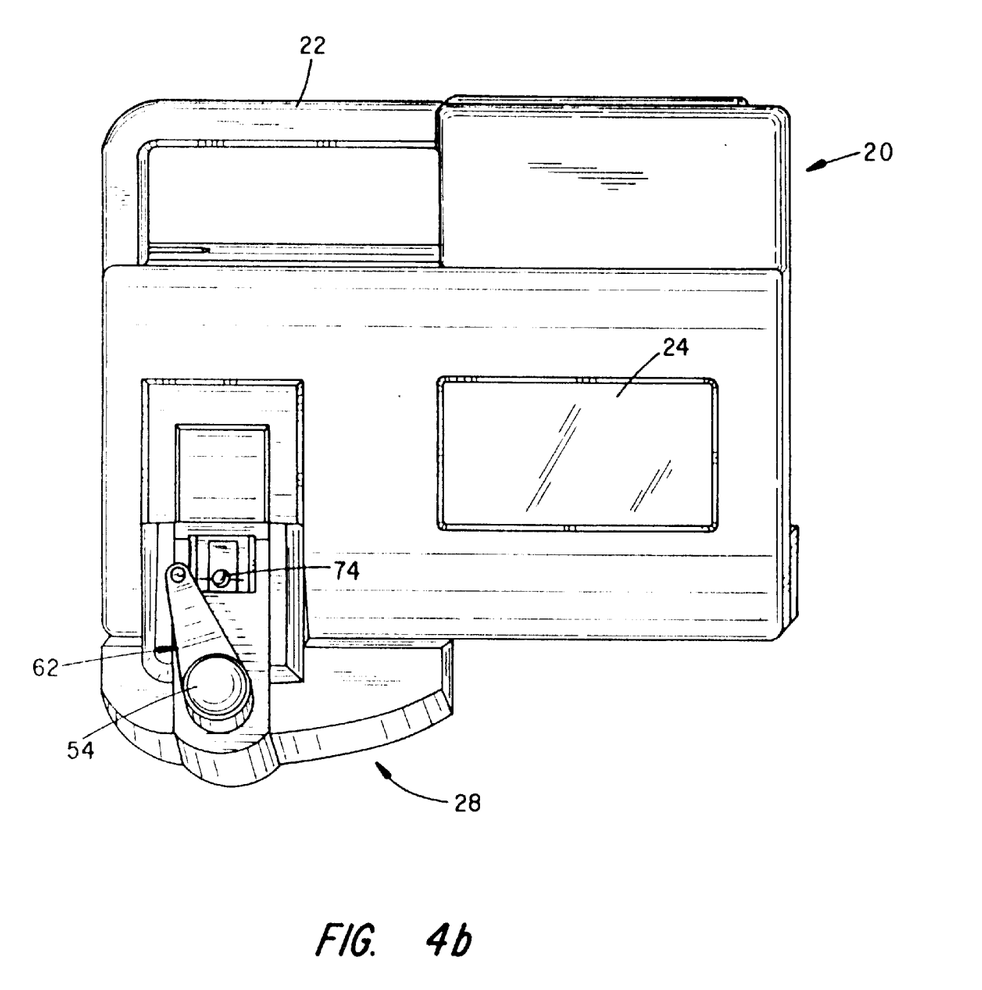

As can be appreciated from the figures and, particularly, from FIGS. 4a and 4b, the lower surface portion 67 of the nozzle 60 containing downward directed fluid outlet 69 is in alignment with the sample and flush port 74 in FIG. 4a and is rotated to the left in FIG. 4b exposing the sample port for receiving a sample. A mechanical tab (not shown) disables and prevents reciprocation of the pump 48 when the arm is displaced from the location at which the nozzle is nested in the sample port 74.

The attributes of the arm-carried flush/recalibration material are two-fold. It allows the flush and calibration fluid to be pumped directly into the sample port to displace tested sample and renew calibration fluid over the sensors for the next test sample. It also serves to cover and protect the sample port from contamination between tests as the spring 68 holds the surface 67 resiliently against the top of sample port 74.

Figure 5A:
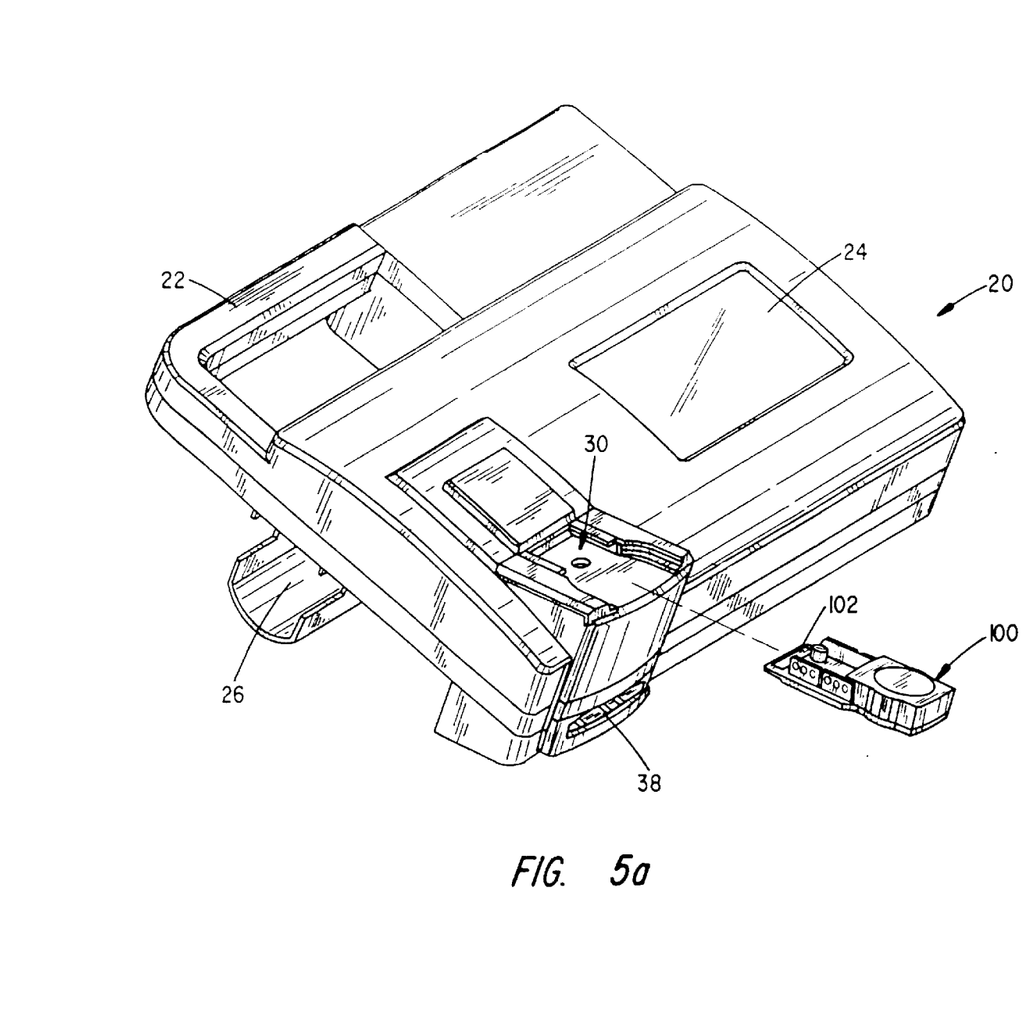
FIGS. 5a and 5b are fragmentary perspective views that illustrate the portable analytical device of FIG. 1 interchangeably employing a single-use analytical cartridge shown respectively in a separated and plugged-in mode.
Figure 5B:
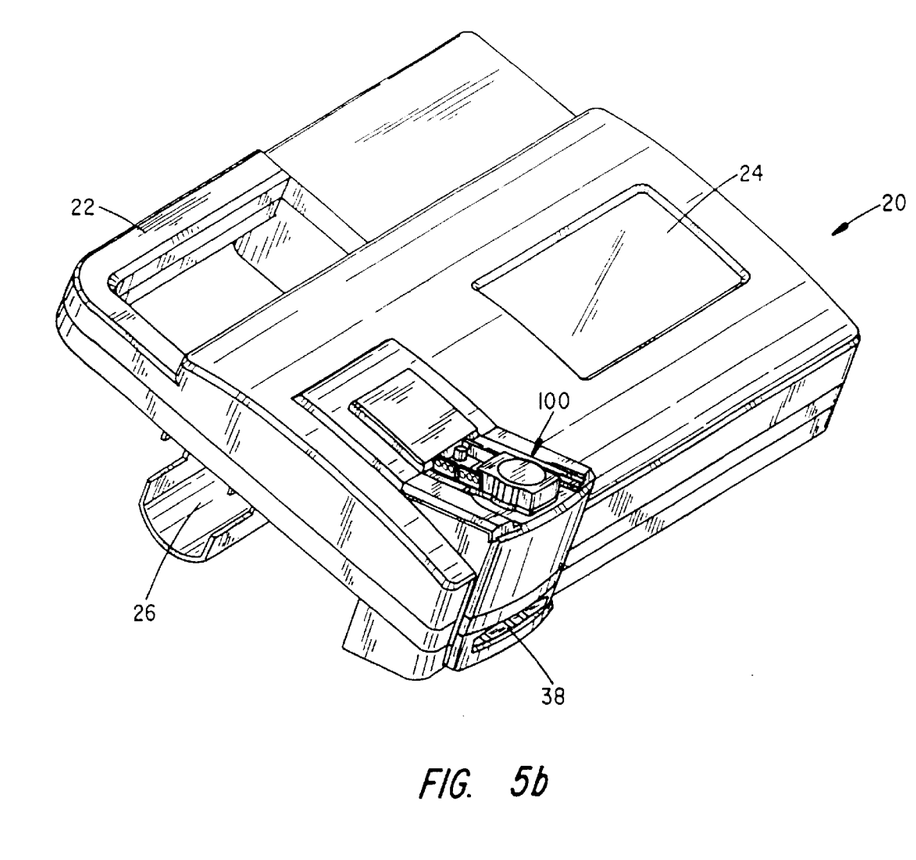

FIGS. 5a and 5b illustrate the use of the portable analytical device 20 with a conventional single-use cartridge 100 as interchangeably usable with the multiple-use modular test system 28. The cartridge 100 contains an identical connection protrusion section 102 which plugs into the same cartridge receptacle 30 as the multiple-use module at 37. FIG. 5a shows the cartridge 100 removed from the portable analyzer and FIG. 5b shows the cartridge plugged into the analyzer in the testing mode. This illustrates the complete interchangeability of the single-use and multiple-use systems.

While the system of plug in, multiple-use module 28 may be designed to conduct any reasonable number of tests, 25 is a typical contemplated average number for each unit. In operation, the modular testing system 28 is plugged into the portable analyzer 20. When the first sample is to be tested, the arm 62 is shifted, removing the nozzle 60 from the sample port so that a syringe can be used to inject the sampled blood or other fluid to be tested into the sample port. The system is designed to automatically calibrate all of the sensors and thereafter quickly analyze and determine the results for a sample. After the first and each ensuing sample is tested, the pump operating button 54 is depressed to inject fluid, displace and rinse away the previous sample and re-establish calibration fluid over the plurality of sensors in the cartridge. The resilient nozzle system protects the sample port from contamination between sample injections.

This invention has been described herein in considerable detail in order to comply with the Patent Statutes and to provide those skilled in the art with the information needed to apply the novel principles and to construct and use such specialized components as are required. However, it is to be understood that the invention could be carried out by specifically different equipment and devices, and that various modifications, both as to the equipment details and operating procedures, can be accomplished without departing from the scope of the invention itself.

What is claimed is:

1. A portable clinical system for providing a rapid electrochemical analysis of biological sera of interest at the point-of-care using a portable analyzer unit and a multi-sensor electrochemical plug-in cartridge analyzing system, the system further comprising;

(a) a self-contained plug-in module including:
(1) a reusable sensor cartridge having an inlet port for receiving fluid samples and flushing and recalibration solution, an outlet drain port, an array of self-calibrating electrochemical sensors and a plurality of electrical terminals for interfacing with the portable analyzer unit; and
(2) an integral flushing system for cleaning and allowing recalibration of said sensor to occur between sample analyses, including a system for supplying a flushing and recalibrating solution to said inlet port for displacing used samples and cleaning said sensors and a plurality of storage reservoirs including a reservoir for retaining used fluid and a reservoir for supplying unused flushing and calibration solution;

(b) matching connection devices on said analyzer unit and said plug-in module for removably attaching said module to said analyzer unit comprising a cartridge connection device provided on said analyzer configured to receive said reusable sensor cartridge of said plug-in module, said connection device on said analyzer also being configured to receive a separate single-use sensor cartridge interchangeably with said plug-in module without modification; and wherein said integral flushing comprises hand-operated infusion pumping system including a pivoting arm carrying an outlet nozzle system, said rotating arm for aligning said nozzle system for infusing solution into said inlet port to displace used sample material and replace same with solution which allows recalibraiton of the sensors for the next sample.

2. The apparatus of claim 1 further comprising closure means in said plug-in module for closing said inlet port and preventing contamination between admission of samples.

3. The apparatus of claim 1 wherein said pivoting arm and outlet nozzle system of said infusion pumping system includes a nozzle having a directed fluid outlet in a generally lower surface that aligns and with closes the inlet port when said nozzle is positioned over said inlet port and wherein said arm pivots to expose the inlet port to allow a sample to be admitted.

4. The apparatus of claim 3 wherein said nozzle is resiliently mounted with respect to said inlet port, said nozzle system including resilient means for urging said lower surface of said nozzle against said inlet port.

5. The apparatus of claim 4 wherein said pivoting arm includes slots and wherein said nozzle is provided with a pair of protruding side tabs designed to snap-fit and be carried in said slots and further comprising a compression spring which urges said nozzle in the direction of said sensor cartridge.

6. The apparatus of claim 5 wherein said infusion pumping system includes a finger-operated reciprocating spray pump.

7. The apparatus of claim 6 further comprising additional stabilizing plug-in device between said analyzer unit and said module to stabilize the attachment of the plug-in module to the analyzer unit.

8. The apparatus of claim 4 wherein said infusion pumping system includes a finger-operated reciprocating spray pump.

9. The apparatus of claim 4 further comprising additional stabilizing plug-in device between said analyzer unit and said module to stabilize the attachment of the plug-in module to the analyzer unit.

10. The apparatus of claim 9 wherein the additional stabilizing plug-in device comprises a snap-fit plug and socket remote from said cartridge connection device.

11. The apparatus of claim 1 wherein said infusion pumping system includes a finger-operated reciprocating spray pump.

12. The apparatus of claim 1 further comprising additional stabilizing plug-in device between said analyzer unit and said module to stabilize the attachment of the plug-in module to the analyzer unit.

13. The apparatus of claim 12 wherein the additional stabilizing plug-in device comprises a snap-fit plug and socket remote from said cartridge connection device.

* * * * *